United States Patent [19]

Kidd et al.

[11] Patent Number: 4,946,386

[45] Date of Patent: Aug. 7, 1990

[54] ORTHODONTIC O-RING DISPENSER AND METHOD OF MAKING

[75] Inventors: Patrick D. Kidd, San Dimas; Terry L. Sterrett, Long Beach, both of Calif.

[73] Assignee: Ormco Corporation, Glendora, Calif.

[21] Appl. No.: 204,635

[22] Filed: Jun. 9, 1988

[51] Int. Cl.⁵ ............................................... A61C 3/00
[52] U.S. Cl. ........................................ 433/18; 433/11; 206/820
[58] Field of Search ................... 433/11, 18; 206/820

[56] References Cited

U.S. PATENT DOCUMENTS

| | | | |
|---|---|---|---|
| 3,193,094 | 7/1965 | Schulstad | 433/149 |
| 3,903,601 | 9/1975 | Anderson et al. | 433/18 |
| 4,038,753 | 8/1977 | Klein | 433/18 |
| 4,106,374 | 8/1978 | Dragan | 433/4 |
| 4,217,686 | 8/1980 | Dragan | 433/4 |
| 4,330,271 | 5/1982 | Anderson | 433/18 |

*Primary Examiner*—John J. Wilson
*Attorney, Agent, or Firm*—Marjama & Pincelli

[57] ABSTRACT

A device for dispensing elastomeric orthodontic appliances. The device has a mounting section having a rigid support structure and an outer layer. The outer layer has integrally formed therewith a plurality of orthodontic appliances detachably connected thereto. The outer layer and appliances are made of a material having a stiffness substantially less than that of the support structure. The device also has a finger gripping section attached at one end of the mounting section and preferably made integral with the rigid support structure.

26 Claims, 2 Drawing Sheets

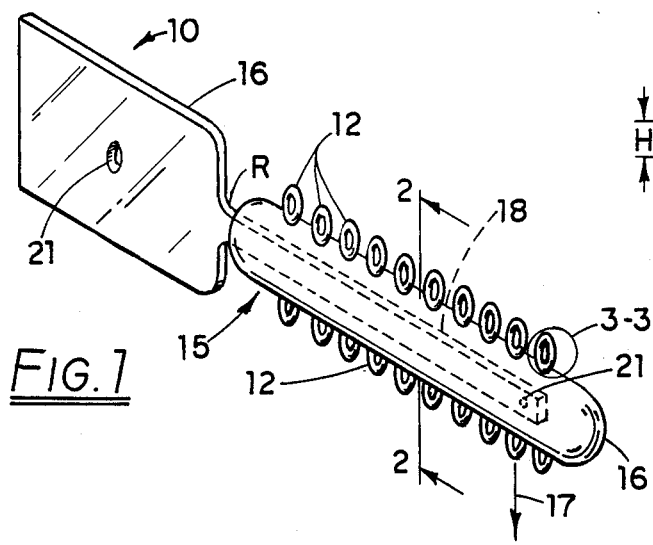
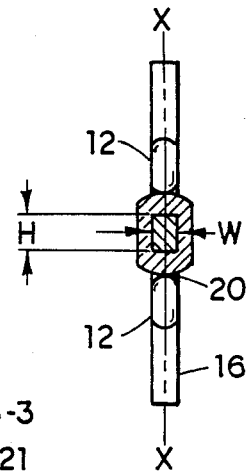
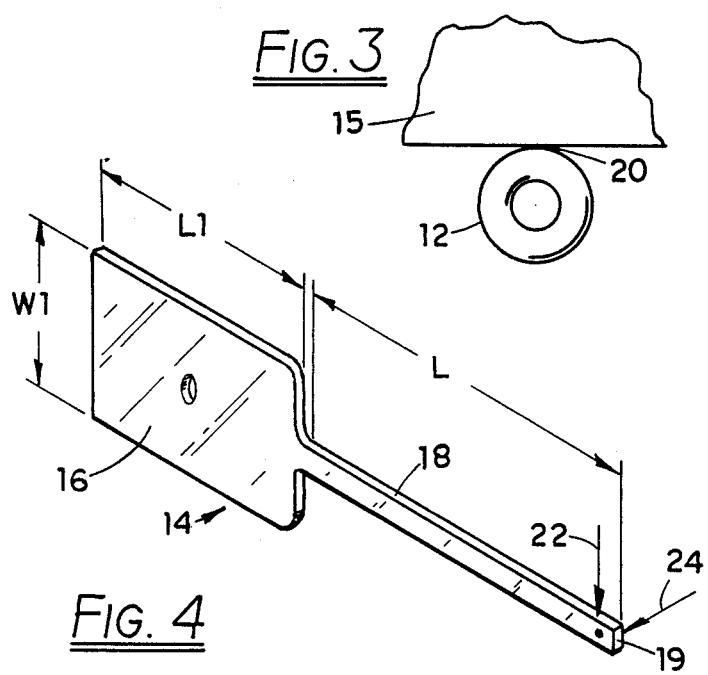
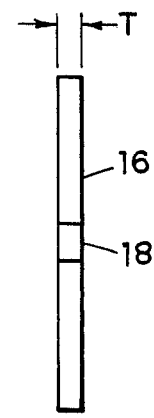

ORTHODONTIC O-RING DISPENSER AND METHOD OF MAKING

BACKGROUND OF THE INVENTION

This invention relates to a device for dispensing orthodontic elastomeric appliances. The present invention is particularly suited for dispensing orthodontic appliances such as orthodontic O-rings and dental wedges.

Prior art orthodontic dispensing appliances are illustrated by U.S. Pat. Nos. 3,193,094; 4,038,753; and 4,217,686. The prior art devices disclosed in these patents are made of the same material as the product being dispensed which is typically of a relatively soft elastomeric material. In todays orthodontic procedures, a strong concern and effort has been made to maintain the aseptic qualities of the orthodontic appliance prior to placement on the patient, and to minimize the possiblity of cross-contamination that may occur during dispensing. Due to the flexible nature and manner of dispensing the appliances of the prior art, at least some manipulation of the dispensing device within the hands of the user is generally required to dispense the appliances. The handling of the dispensing device typically occurs in the vicinity of the appliances to be dispensed and thus subjects these appliances to potential contamination.

Applicant has invented an improved dispensing device wherein the orthodontic appliances are easily dispensed, while at the same time improving the aseptic qualities of the appliances being dispensed.

SUMMARY OF THE INVENTION

In one aspect of the invention, there is provided a dispensing device for dispensing elastomeric orthodontic appliances. The device comprises a mounting section about which the appliances are arranged and a finger gripping section. The mounting section is a composite structure including a rigid support structure and an outer layer laminated to the support structure. The outer layer has integrally formed therewith a plurality of the orthodontic appliances detachably connected thereto. The appliances are made of an elastomeric material having a stiffness substantially less than that of the support structure.

In another aspect of the present invention, there is provided an improved orthodontic dispensing device. A rigid support structure and a finger gripping section are integrally formed. The rigid support structure is placed in a mold and an outer layer is provided on the support structure. The outer layer has a plurality of detachable orthodontic appliances formed therewith; and the layer and appliances are made of a material substantially more elastic than the support structure.

DESCRIPTION OF THE DRAWINGS

FIG. 1 is a perspective view of a dispensing device made in accordance with the present invention;

FIG. 2 is an enlarged cross sectional view of the dispensing device of FIG. 1 made taken along line 2—2;

FIG. 3 is an enlarged partial view of the device of FIG. 1 illustrated by circle 3—3;

FIG. 4 is a perspective view of the rigid support structure of the device of FIG. 1;

FIG. 5 is a side view of the rigid support structure of FIG. 4;

DETAILED DESCRIPTION

Figure 6:
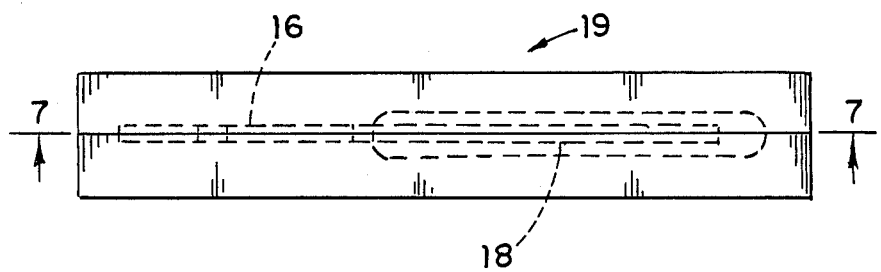
FIG. 6 is a top plan view of the rigid support structure in a mold for forming outer layer.

Referring to FIG. 1-3, there is illustrated an orthodontic dispensing device 10 made in accordance with the present invention. The dispensing device 10 in the particular embodiment illustrated, dispenses a plurality of individual orthodontic O-rings 12 for ligating of orthodontic brackets to orthodontic arch wires. The orthodontic dispensing device 10 comprises a rigid support structure 14 (see FIG. 4) and outer layer 15 secured thereto. The outer layer 15 has a plurality of detachably connected O-rings 12 integrally formed therewith.

The rigid support structure 14 comprises a finger gripping section 16 disposed at the one end and an elongated dispensing support section 18 extending from one end of gripping section 16. Preferably as illustrated, the part of support structure 14 wherein support section 18 merges with gripping section 16 is provided with a round fillet having an appropriate radius R to strengthen the support structure in this area. In the particular embodiment illustrated, the radius R is approximately 0.238 cm. The support structure 14 is designed to have a sufficient degree of rigidity to permit easy removal of orthodontic O-rings 12 from the appliance 10 by pulling them off with a hemostat or other device typically used for removing 0-rings from prior art type devices.

Figure 7:
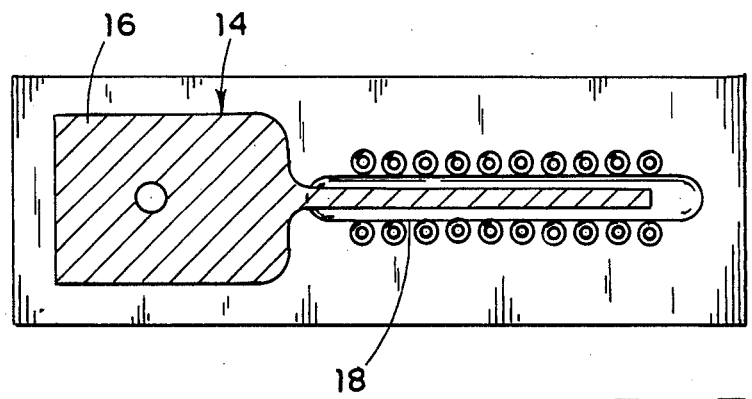
FIG. 7 is a cross-sectional view of the mold of FIG. 6 prior to forming the outer layer.

In the manufacture of the dispensing device 10 of the present invention, the support structure 14 is preferably molded as a single integral piece. Thereafter, an outer layer 15 is secured to support structure 14. Preferably, the molded support structure 14 is placed in a second mold 19 wherein the outer layer 15 is injection molded over the support section 18. Applicants have found that due to the relative small size of support structure 14 and outer layer 15 that locating pins (see FIGS. 6 and 7) be placed in the second mold which mates with openings 21 previously formed in support structure 14 (which has been previously provided) so that an uniform outer layer 15 is formed. Preferably, one opening 21 is provided in gripping section 16 approximately in the middle and a second opening 21 is provided near the outer end 19 of support section 18. The opening 21 in gripping section 16 is about 0.317 cm and the opening in support section 18 is about 0.158 cm. The dash lines in FIG. 1 illustrate the outer configuration around which cover layer 15 is molded. The outer layer 15 is made of a material which has a melting point lower than support structure 14 to maintain its rigidity during molding of the outer layer thereto. Preferably, support structure 14 has a melting point of at least 30° C. above the melting point of outer layer 15. The melting point of the support structure 14 should not be too much higher than outer layer 15, so that bonding of outer layer 15 to support structure 14 is maintained. Preferably, the melting point of support structure 14 is no greater than 130° C. above the melting point of outer layer 15. In the embodiment illustrated, support structure 14 is made of a glass filled polycarbonate. An example of a suitable polycarbonate that may be purchased is a natural glass filled polycarbonate sold by the Thermofill Company (Product Code R-20-FG-0100).

The support structure 14 is preferably made of a plastic material having biocidal properties. Making support structure 14 of a biocidal material contributes to minimizing the amount of cross contamination and/or propagation of contaminents from the gripping section to the orthodontic O-rings 12. The biocidal properties may be obtained by addition of additives to the polycarbonate, such as those illustrated in U.S. Pat. Nos. 4,404,296; 4,542,169; 4,677,443; 3,006,870; 3,476,854; 3,531,431; 4,012,351; and 4,263,424.

It is to be understood that the outer cross-sectional configuration of outer layer 15 may take any shape desired. In the particular embodiment illustrated, the outer layer 15 completely surrounds the cross sectional shape of the support section 18 so as to provide a sleeve around support section 18. The support structure 14 is preferably made of a plastic material. The device 10 preferably has a substantially constant thickness along the length of support section 18, preferably in the range of 0.08 cm to 0.25 cm. In the embodiment, illustrated, the support section 18 has a thickness of about 0.13 cm.

The outer layer 15 has a plurality of elastomeric orthodontic O-rings 12 integrally formed therewith and is made of an appropriate elastomeric material commonly used for orthodontic O-rings. In the particular embodiment illustrated, outer layer 15 and O-rings 12 are made of a thermoplastic polyurethane, for example, Dow Pellethane 2363-80A. Outer layer 15 and of course integrally formed O-rings 12 are made of material having a flexural modulus substantially less than support structure 14, preferably in the range of about 20 MPa to 70 MPa.

The O-rings 12 are detachably connected to outer layer 15 such that O-rings 12 can be easily removed by a hemostat or other device typically used. The connection 20 is such that a relatively small amount of force is required to remove the individual O-rings. Generally, the force required is no more than 0.5 kilograms, preferably between 0.1 kilograms to 0.25 kilograms. The O-rings 12 are preferably disposed adjacent support section 18, such that none are secured to outer layer 15 beyond the outer end 19 of support section 18. It is important to provide the degree of stiffness so that the O-rings can be easily detached from outer layer 15.

The dispensing of O-rings 12 is a relatively simple procedure. The user grasps the gripping section 16 between his or her fingers on one hand. Using a hemostat or other pulling device in the other hand, grasp one of the O-rings 16 in the hemostat and pulls in a direction (see arrow 17 in FIG. 1) substantially perpendicular to the support section 18, and thus removes the O-ring 16.

The rigid support structure 14 provides the appropriate rigidity necessary to allow removal of the orthodontic O-ring 12 from the dispensing device 10. For the purposes of the present invention, the rigidity of the support structure 14, and in particular the support section 18, should be such as to resist any substantial deformation of support section 18 when the gripping section 16 is securely held. Applicants have found that the support section 18 should have a flexural modulus no less than about 4.0 GPa as measured perpendicular thereto at the furthest unsupported end as illustrated by arrows 22 and 24 in FIG. 4, preferably no less than 5.0 GPa. In order to provide the appropriate rigidity, support structure 14 and more particularly the support member 18 is made of a material having a cross sectional configuration to resist the forces illustrated by arrows 22 and 24 in FIG. 4. In the particular embodiment illustrated, the cross sectional configuration of support member 18 is substantially rectangular and has a height H of approximately 0.25 cm, a width W of about 0.207 cm, and a length L of approximately 4.5 cm. In the particular embodiment illustrated, the support structure 14 is made of a polycarbonate having a modulus of elasticity preferably greater than 7.0 GPa. It is quite apparent that the desired rigidity can be obtained by varying the cross sectional shape and configuration to provide the appropriate rigidity desired. This rigidity can also be increased by making support structure 14 of a material having relatively high stiffness.

The gripping section 16 is integrally formed with the support section 18 and preferably takes the configuration of a plate whereby the user can simply hold gripping section 16 between his or her fingers. In the particular embodiment illustrated, the gripping section 16 is substantially rectangular in configuration, however, any other desired configuration may be used. The only specific requirement for the configuration of gripping section 16 is that the user can easily grasp it between his or her fingers. In the particular embodiment illustrated, the gripping section 16 has a width W1 of approximately 2.16 cm, a length L1 of about 2.54 cm, and a thickness T of about 0.51 cm.

In the preferred form of the present invention, the outer layer 15 is provided with a sufficient plurality of O-rings 12 needed to treat a single patient. This minimizes or avoids the problem of having too many O-rings on dispensing device 10 which is used on a second patient at a later point in time. This minimizes the potential contamination resulting the time difference between dispensing of the O-ring's and any potential storage problems that exists between uses. Applicants have found that for cases involving the upper or lower teeth, approximately 10 to 12 O-rings need be provided, and if both lower and upper teeth are involved, then about 20 to 22 O-rings are necessary. As in the preferred embodiment illustrated, the O-rings are disposed along the support section 18 such that the O-rings are substantially in the same plane as the vertical axis x—x of the support section 18 as illustrated in FIG. 2.

A particularly important advantage of the present invention is that the means for holding the dispenser 10 is disposed distant from the area from which holds and dispenses the O-rings 12. This minimizes any potential contamination which may result from the user holding the dispenser in his hand, as in the prior art. Prior art devices, as previously noted, require that a substantial portion of the dispenser be held within the hand for direct contact hereon. In the present invention, the means for holding the dispenser is remote and distant from the O-ring dispensing area. Furthermore, since the gripping portion 16 may be made of a biocidal and/or fungicidal material, this further minimizes any potential contamination portion held by the user being transmitted directly to the O-rings.

It is to be understood that various changes or modifications, for example, while the preferred material that support structure 14 be made of plastic, it can be made of any other rigid material desired, such as aluminum, stainless steel, etc. Additionally, the support is not necessarily molded. It can be stamped, cast, cut, or formed in any other manner desired. While molded outer layer 15 has certain distinct advantages, the outer layer 15 may be pre-formed and secured to support structure 14 in any manner desired, for example, solvent bonding, cementing, or by pop rivets.

It is to be understood that various other modifications may be made without departing from the scope of the present invention. The scope of protection being limited only by the attached claims.

What is claimed is:

1. A dispensing device for dispensing elastomeric orthodontic appliances comprising:
   an integral rigid support structure having an elongated support section at one end and a finger gripping section disposed at the other end of said support structure, said support section having an outer layer secured thereto, said outer layer having a plurality of orthodontic appliances integrally formed therewith which are detachably connected to said outer layer, said rigid support structure being made of a material having a stiffness substantially greater than said outer layer such that said orthodontic appliance may be removed therefrom while holding said finger gripping section.

2. A dispensing device for dispensing elastomeric orthodontic appliances according to claim 1 wherein said finger gripping section is in a plate configuration.

3. A dispensing device for dispensing elastomeric orthodontic appliances according to claim 2 wherein said appliance lies in the same plane as said plate.

4. A dispensing device for dispensing elastomeric orthodontic appliances according to claim 1 wherein said elongated support section has a substantially rectangular cross-sectional configuration.

5. A dispensing device for dispensing elastomeric orthodontic appliances according to claim 4 wherein said O-rings are disposed on the surface of said outer layer adjacent said short sides of said cross-sectional configuration.

6. A dispensing device for dispensing elastomeric orthodontic appliances according to claim 1 wherein said device is designed to hold a sufficient number of O-rings to treat a single patient's needs.

7. A dispensing device for dispensing elastomeric orthodontic appliances according to claim 1 wherein said elongated support section and said finger gripping section are integrally formed and made of a biocidal material.

8. A dispensing device for dispensing elastomeric orthodontic appliances according to claim 1 wherein said rigid support structure is made of a polycarbonate material and said outer layer is made of thermoplastic polyurethane material.

9. A dispensing device for dispensing elastomeric orthodontic appliances according to claim 1 wherein said outer layer comprises a sleeve having a substantially constant thickness in the range of approximately 0.08 to 0.25 cm.

10. A dispensing device for dispensing elastomeric orthodontic appliances according to claim 1 wherein said elastomeric orthodontic appliances are orthodontic O-rings.

11. A dispensing device for dispensing elastomeric orthodontic appliances according to claim 1 wherein said rigid support structure has a flexural modulus no less than about 4.0 GPa.

12. A dispensing device for dispensing elastomeric orthodontic appliances according to claim 11 wherein said outer layer is made of a material having a flexural modulus in the range of about 20 MPa to 70 MPa.

13. A dispensing device for dispensing elastomeric orthodontic appliances comprising:
   an integral rigid support structure having a rigid mounting section having an elongated support section at one end and a finger gripping section disposed at the other end of said support structure, said support section having an outer layer molded thereto, said outer layer having a plurality of orthodontic elastomeric appliances integrally formed therewith which are detachably connected thereto, said rigid support structure being made of a material having a stiffness substantially greater than said outer layer such that said orthodontic appliance may be removed therefrom while holding said finger gripping section.

14. A dispensing device for dispensing elastomeric orthodontic appliances according to claim 13 wherein said finger gripping section is in a plate configuration.

15. A dispensing device for dispensing elastomeric orthodontic appliances according to claim 13 wherein said elongated support structure has a substantially rectangular cross-sectional configuration.

16. A dispensing device for dispensing elastomeric orthodontic appliances according to claim 15 wherein said O-rings are disposed on the surface of said outer layer adjacent said short sides of said cross-sectional configuration.

17. A dispensing device for dispensing elastomeric orthodontic appliances according to claim 13 wherein said device is designed to hold a sufficient number of O-rings to treat a single patient's needs.

18. A dispensing device for dispensing elastomeric orthodontic appliances according to claim 13 wherein said elongated support section and said finger gripping section are integrally formed and made of a biocidal material.

19. A dispensing device for dispensing elastomeric orthodontic appliances according to claim 13 wherein said rigid support structure is made of a polycarbonate material and said outer layer is made of thermoplastic polyurethane material.

20. A dispensing device for dispensing elastomeric orthodontic appliances according to claim 13 wherein said outer layer comprises a sleeve having a substantially constant thickness in the range of approximately 0.08 to 0.25 cm.

21. A dispensing device for dispensing elastomeric orthodontic appliances according to claim 13 wherein said appliance lies in the same plane as said plate.

22. A dispensing device for dispensing elastomeric orthodontic appliances according to claim 13 wherein said elastomeric orthodontic appliances are orthodontic O-rings.

23. A dispensing device for dispensing elastomeric orthodontic appliances according to claim 13 wherein said rigid support structure has a flexural modulus no less than about 4.0 GPa.

24. A dispensing device for dispensing elastomeric orthodontic appliances according to claim 13 wherein said outer layer is made of a material having a flexural modulus in the range of about 20 MPa to 70 MPa.

25. A method of making an orthodontic dispensing device comprising a rigid support structure having a finger gripping section, elongated support section, and an outer layer molded around said elongated support section having a plurality of orthodontic appliances integrally formed therewith, comprising the steps of:
   forming said rigid support structure of a material having a stiffness such that said orthodontic structure may be removed therefrom while holding said finger gripping section;
   placing said rigid support structure in a mold;
   forming said outer layer on said elongated support section in said mold.

26. A method according to claim 25 further comprising the steps of
   providing aligning opening in rigid support structure;
   providing aligning pins in said mold for placement in said aligning openings so as to positively position said rigid structure in said mold during formation of said outer layer.

* * * * *